United States Patent [19]
Hughes

[11] Patent Number: 5,351,643
[45] Date of Patent: Oct. 4, 1994

[54] HIGH DENSITY REARING SYSTEM FOR LARVAE

[75] Inventor: Patrick R. Hughes, Ithaca, N.Y.

[73] Assignee: Boyce Thompson Institute for Plant Research, Inc., Ithaca, N.Y.

[21] Appl. No.: 93,982

[22] Filed: Jul. 19, 1993

Related U.S. Application Data

[63] Continuation-in-part of Ser. No. 62,417, May 13, 1993, abandoned, which is a continuation-in-part of Ser. No. 989,103, Dec. 11, 1992, abandoned.

[51] Int. Cl.$^5$ ............................................. A01K 67/04
[52] U.S. Cl. .................................................. 119/6.5
[58] Field of Search ....................... 119/6, 6.5, 15, 21, 119/35, 37

[56] References Cited

U.S. PATENT DOCUMENTS

| | | | |
|---|---|---|---|
| 2,670,562 | 3/1954 | Gould | 119/6.5 |
| 4,212,267 | 7/1980 | Patterson | 119/6.5 |
| 5,113,799 | 5/1992 | Carr et al. | 119/6.5 |
| 5,178,094 | 1/1993 | Carr et al. | 119/6.5 |

OTHER PUBLICATIONS

Wood, H. A. et al, 1991, Annu. Rev. Microbiol, Genetically Engineered Baculoviruses as Agents for Pest Control, 45: 69–87.
Eating Bugs in the Big Apple, ESA Newsletter, Aug. 1992 vol. 15, No. 8.
Singh, P. and Moore, R. F., Handbook of Insect Rearing vol. I 1985.
Singh, P. and Moore, R. F., Handbook of Insect Rearing vol. II 1985.
Guy, R., et al, Insect Attractants, Behavior, and Biology Res. Lab. and Dept. of Entomology & Nematology, Univ. of Florida, pp. 487–495.
Leppla, N. et al, 1984, Advances and Challenges in Insect Rearing, U.S. Dept. Tech. Bull. pp. 248–254.
Vail, P. et al, Environmental Entomology, vol. 2., No:3, New Procedures for Rearing Cabbage Loopers and Other Lepidopterous Larvae for Propagation of Nuclear Polyhedrosis Viruses, pp. 339–344.
Henneberry, T. et al, 1966, Academic Press, Cabbage Loopers pp. 461–478.
Lawson, F. et al, Facilities For Insect Research and Prod., U.S. Dept. of Agric. Tech. Bull., Small Plant for Production of Trichoplusia NPV, 1987, pp. 37–39.
Luckow, V., 1990, McGraw Hill, Cloning and Expression of Heterologous Genes in Insect Cells with Baculivirus Vectors, pp. 97–152.

*Primary Examiner*—Thomas Price
*Attorney, Agent, or Firm*—Barnard, Brown & Michaels

[57] ABSTRACT

Method and apparatus for rearing insects is disclosed. Information concerning the physical and dietary needs of the insect as well as behavioral characteristics are utilized to maximize the number of larvae reared per unit surface area of diet and per unit of rearing area while minimizing the amount of labor and materials required. An enclosed rearing unit is provided which can be located within an appropriate environment for rearing the insects. There are three sections within the rearing unit: 1) a diet space, 2) a larval space, and 3) a frass space. The diet space includes an appropriate diet medium for the insects. The larval space is located below the diet space and includes a series of vertical partitions perpendicular to and in contact with or nearly in contact with the diet medium such that the insect larvae are able to disperse themselves over the partitions. The frass space is located below the larval space such that any frass collects within the frass space as it is produced and does not interfere with the larval space or the diet space. The rearing system can further include an emergence pan including an outlet for allowing emerging adults to enter an oviposition cage. The emergence pan replaces the frass collection pan when all of the larvae have pupated. The rearing unit is turned upside down such that the emergence pan is located above the larval space and the diet space.

20 Claims, 7 Drawing Sheets

HIGH DENSITY REARING SYSTEM FOR LARVAE

This application is a continuation-in-part of co-pending application Ser. No. 08/062,417, filed May 13, 1993, now abandoned, which is a continuation-in-part of 07/989,103, filed Dec. 11, 1992, now abandoned.

FIELD OF INVENTION

This invention relates to method and apparatus for rearing insects from eggs to pupae or adults, and more particularly relates to rearing insects at high density with low labor and material cost per insect.

BACKGROUND OF THE INVENTION

There is increasing need for an economical means for mass rearing of many lepidopteran species for commercial purposes.

Large numbers of larvae of various species are needed for the production of a variety of traditional biological control agents (predators, parasites, and parasitoids), which are taking on a greater importance in world agriculture. The sterile male technique for insect control requires economical production of great numbers of individuals for sterilization and release.

With the development of the baculovirus expression vector system [e.g., V. A. Luckow, "Cloning and expression of heterologous genes in insect cells with baculovirus vectors", In Recombinant DNA Technology and Applications, C. Ho. A. Prokop and R. Bajpai (eds.), pp. 97-152, McGraw-Hill, New York, 1990], insect larvae, principally lepidopterans, are being considered as a central part of systems for producing commercial quantities of many pharmaceutically important proteins.

Presently, insect viruses, primarily baculoviruses infecting lepidopterous pests, are being genetically engineered and developed as commercial biorational pesticides (H. A. Wood and R. R. Granados, "Genetically engineered baculoviruses as agents for pest control", Ann. Rev. Microbiol., 45: 69-87, 1991); the cost of their production is determined principally by the cost of rearing the insects used for their propagation.

Insects are even being considered as a valuable protein source themselves (e.g., "Eating bugs in the Big Apple", ESA Newsletter, 15(8), August 1992).

Current methods for rearing lepidopterous insects are extremely varied, depending on the species, the laboratory, and the purposes for which the insects are being reared. The two-volume series edited by Pritam Singh and R. F. Moore (Handbook of Insect Rearing, Volumes I and II, Elsevier Science Publishers, 1985), in which methods being used to rear 38 species of lepidopterans are described, is perhaps the most comprehensive treatment in recent years of methods for rearing these insects. In developing the invention described in this application, which particularly concerns the means by which the insects are reared from egg through the larval and pupal stages to adult, the cabbage looper, *Trichoplusia ni*, was used as a type species, and the many different methods that have been used for the mass-rearing of this species are typical of those used for lepidopterans in general [for reviews see: N. C. Leppla, P. V. Vail, and J. R. Rye, 1984, "Mass Rearing the Cabbage Looper, *Trichoplusia ni*", In Advances and Challenges in Insect Rearing, E. G. King and N. C. Leppla (eds.), U. S. Dept. Agric. Tech. Bull. pp. 248-254; R. H. Guy, N. C. Leppla, J. R. Rye, C. W. Green, S. L. Barrette, and K. A. Hollien In Handbook of Insect Rearing, P. Singh and R. F. Moore (eds.), Vol. II, 1985, pp. 487-497].

A great variety of containers have been used for the larval stage. P. V. Vail, S. J. Anderson and D. L. Jay ("New procedures for rearing cabbage loopers and other lepidopterous larvae for propagation of nuclear polyhedrosis viruses", 1973, Environ. Entomol. 2, pp. 339-344) described the use of paraffin-coated paper bags (16×19.5×32 cm deep) with 500 ml of diet and 250 eggs/bag yielding 190 pupae; these bags were hand-coated with paraffin and the thickness of the coating was critical to their success (the diet "sweated excessively" if the coating was too thick and dried excessively if the coating was too thin). The most frequently used type of larval rearing container has been paraffin-coated paper cups. T. J. Henneberry and A. N. Kishaba ["Cabbage Loopers", in Insect Colonization and Mass Rearing, C. N. Smith (ed.), Academic Press, 1966, pp. 461-478] described the use of 6- or 8-oz (ca. 178 to 237 ml) cups for rearing the larvae to pupation and recommended a maximum of 24 larvae/cup with 70-80 ml of diet. Such cups were used in a small-scale virus production plant described by F. R. Lawson anti R. L. Headstrom ("Small plant for production of *Trichoplusia ni* NPV", In Facilities For Insect Research and Production", N. C. Leppla and T. R. Ashley (eds.), U.S. Dept. of Agric. Tech. Bull. 1576, 1978, pp. 37-39. Plastic containers (30.5×30.5×12.7 cm deep I.D.) were described for rearing the larvae by R. H. Guy, N. C. Leppla, J. R. Rye, C. W. Green, S. L. Barrette, and K. A. Hollien ["*Trichoplusia ni*", In Handbook of Insect Rearing, P. Singh and R. F. Moore (eds.), Vol. II, 1985, pp. 487-497]; each of these containers was seeded with 300-350 eggs with 1 liter of diet and yielded ca. 240-280 pupae.

When the insects have pupated in the cups, the pupae are typically removed by hand, subjected to a surface-sterilization procedure, and placed into some type of emergence cage distinctly different from the larval rearing container. For example, Henneberry and Kishaba collected the pupae from the larval rearing cartons, soaked them for 10-15 minutes in 1-1.5% sodium hypochlorite, rinsed them several times in tap water, placed then, on paper toweling to dry, and then placed them in emergence cages made from 1-gal cylindrical cardboard containers. The method of Guy et al. contained the same steps with the addition of using forceps to remove all debris after the pupae dried, counting the pupae, and weighing a random sample.

The cost associated with most commercial uses of lepidopterous larvae, such as production of viruses, parasites, etc., is largely that of rearing the larvae. The above methods generally are too costly to make the products commercially practical and/or economically competitive with other options in the present-day market. They typically require 3-4 ml of diet/starting individual insect and require a high amount of area per initial insect and/or have low yields of late instars (e.g., 35 cm³/starting individual and 80% yield by the method of Guy et al. or 40 cm³/starting individual and 76% yield by the method of Vail et al.). Also, a considerable amount of labor is required through the complete rearing cycle, such as handling large numbers of small rearing units (i.e., cups), collecting and sterilizing pupae, and transferring pupae into emergence cages. Furthermore, considerable difficulty has been encountered in controlling the moisture/humidity in the rearing containers, especially creating problems with controlling fungi and bacteria.

SUMMARY OF THE INVENTION

The present invention includes method and apparatus for rearing insect larvae. An enclosed rearing unit is provided which can be located within an appropriate environment for rearing the insects. There are three sections within the rearing unit: 1) a diet space, 2) a larval space, and 3) a frass space. The diet space includes an appropriate diet medium for the insects. The larval space is located below the diet space and includes larval attaching surfaces throughout the larval space such that the larvae can attach themselves to the surfaces and eat the diet. The larval attaching surfaces can be provided by edge posts wherein the larvae will attach themselves on the edges of the posts. The larval attaching surfaces could also be provided by a series of vertical partitions perpendicular to and in contact with or nearly in contact with the diet medium such that the insect larvae are able to disperse themselves over the partitions. The frass space is located below the larval space such that any frass collects within the frass space as it is produced and does not interfere with the larval space or the diet space.

A maximum larval density is determined for the insect within the rearing unit at the desired stage of development or at the last instar of larval development, whichever occurs first wherein the maximum larval density is based upon the behavior of the insect larvae and the amount of surface area of the partitions within the larval space. Eggs of the insects are placed within the rearing unit and allowed to hatch and the larvae are allowed to grow to the desired stage of development such that the amount of eggs placed within the rearing unit is dependant upon the maximum larval density for the insect. As the eggs hatch the emerging larvae are able to move into the larval space of the rearing unit.

The frass space can be provided with means for controlling air passage through the rearing unit such that the insect larvae can not escape through the means for controlling air passage yet excess moisture from the frass can escape. The rearing unit can include a removable frass collection pan. The frass collection pan is replaced with an emergence pan including an outlet for allowing emerging insects to enter an oviposition cage. If the larvae are allowed to pupate, the rearing unit can be inverted when all of the larvae have pupated such that the emergence pan is located above the larval space and the diet space.

The method and apparatus of the present invention teach that, given the proper conditions and container structure which considers both the physical needs and the behavior of the insect, the larvae can be reared at much higher densities on considerably less diet with better control of moisture difficulties and less manual labor. Thus, this invention represents a simple solution to a problem in a manner which is a great improvement over the teachings and expectations of the prior art.

It is therefore an object of this invention to disclose a novel method of rearing insects in high numbers at low cost per animal.

It is further object of this invention to disclose novel apparatus for rearing insects in high numbers at low cost per animal.

Further objects of the invention will be set forth in the description which follows, and will become apparent to those skilled in the art upon examination of the specification or by practice of the invention.

DETAILED DESCRIPTION OF THE INVENTION

Method and apparatus for rearing insects are disclosed. The present invention utilizes previously unrecognized and/or unutilized behavioral characteristics of lepidopterous larvae to maximize the number of larvae reared per unit surface area of diet while minimizing the amount of labor and materials required. It also provides a physical arrangement that allows for easy separation of the insects from frass (excretions from the larvae) and unused diet, if necessary, and allows for greatly improved dissipation of excess moisture generated predominantly in the late larval stage while protecting the diet from early desiccation.

Figure 1:
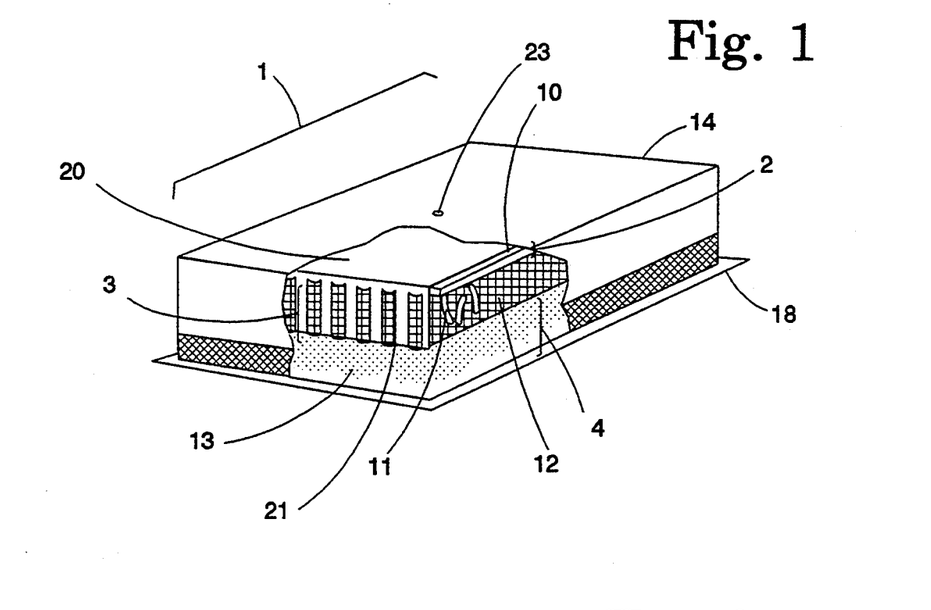
FIG. 1 is a perspective view of one embodiment of a high density rearing unit being used to rear insects for virus production.
Figure 2:
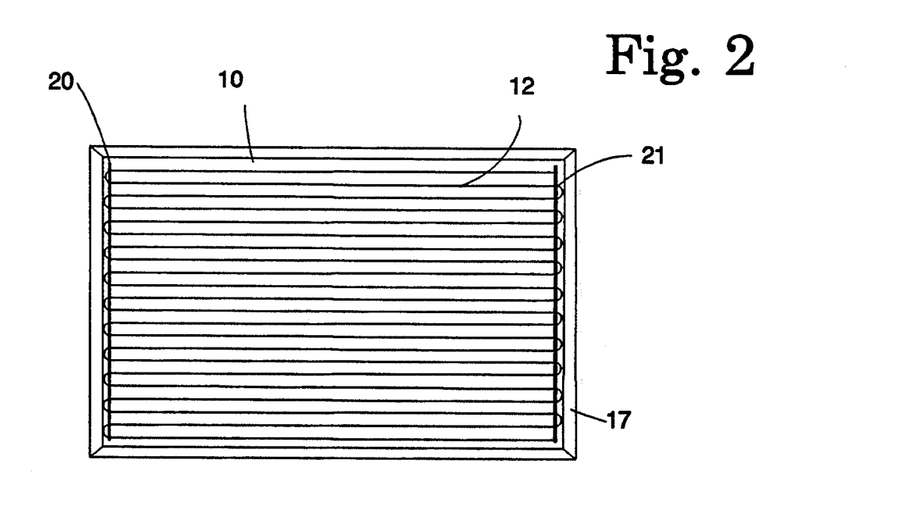
FIG. 2 is a bottom view of one embodiment of a high density rearing unit showing the partitions in detail.

Referring now to FIGS. 1 and 2, the rearing unit 1 consists of areas or general components: the diet space 2, the larval space 3, and the frass space 4 which allows frass to accumulate and dissipate moisture. The diet space 2 contains the diet medium 10 upon which the larvae 11 will feed and is located above the larval space 3; the larval space 3 contains a series of vertical partitions 12 oriented at right angles to and touching or nearly touching the diet medium surface 10 and provides the substrate upon which the larvae 11 can stand while feeding. The frass space 4 is an area below the larval space 3 into which frass 13 drops as it is produced. The sides of this area can be screened and open to air movement, allowing moisture from the frass to dissipate but preventing larval escape.

Overall dimensions of the rearing unit 1 can be varied based on the purpose of the endeavor with no practical lower limit and the upper size limit dependent on provisions for handling. The depth of the diet 10 is selected such that the larvae 11 have sufficient diet 10 to carry them through to the particular stage of interest. The spacing of the partitions 12 is dependent on the minimal distance between larvae 11 of the particular species required to reduce to acceptable levels the degree of interaction between larvae 11, as manifested by such measures as degree of biting/injuring of neighboring larvae 11 or reduced pupal weight; this spacing may be varied according to the species, the stage to which the larvae 11 are to be reared, the purpose for which the larvae 11 are being reared, etc., and, therefore, can be optimized according to the given situation. The partitions 12 can be of any suitable material, depending on the needs, but must be such that larvae 11 of the largest size being reared can easily hold fast to it. To maximize the number of larvae 11 that can be reared in a given area, the width of the partitions 12 needs to be minimized, and the material should be capable of being sterilized if it is not disposable.

The novel discoveries important to this invention are that: 1) for each species there is an average minimal space requirement which increases with age/stage and is maximum in the last instar, 2) when eggs are placed on or near diet, the hatching larvae will move to feed on the diet and will space themselves evenly to feed and grow, 3) given the opportunity, the larvae will self-regulate their spacing to reach or exceed the minimal value, 4) when given vertical surfaces on which they are able to firmly hold, the larvae will align themselves on this surface approximately perpendicular to the die, thus maximizing the number of larvae that can be reared on a given area of diet, 5) when given edge surfaces on which the larvae are able to firmly hold versus flat surfaces, they will attach themselves along the edge surfaces preferentially over the flat surfaces, and 6) the spacing requirement is lost in the prepupal stage.

Moisture control is always an important concern in rearing insects. If the environment is too moist, fungus, mold or bacteria tend to grow. If the environment is too dry, then the diet medium dries out and the larvae starve. While moisture tends to vary greatly during each stage of development, drying seems to be a problem during the egg hatching to early instar stages of development. Screens have been shown in each embodiment of the present invention. Since dryness is generally a problem early in developments, these screens can be sealed off to avoid escape of moisture and/or early instar larvae. As the larvae grow and moisture begins to accumulate the screens are opened as desired to control moisture. The screens could be left entirely open and the rearing units could be used in a room with controlled humidity. These screens can be of a small enough mesh size to avoid escape by early instar larvae, however, once the larvae find a food source (in this case the diet medium) they generally do not venture from it depending upon the species, especially if the units are held in darkness.

Different physical arrangements of the invention were used to rear *T.ni*. Generally, a smaller size was used for rearing relatively low numbers of individuals (500–1000/unit) for colony maintenance and a larger size was used for rearing larger numbers (2500–3000/unit) for virus production. The dimensions of each embodiment shown are included to provide a scale for determining density of larvae or adult production in a given volume of rearing chamber.

Virus Production Unit

Figure 5:
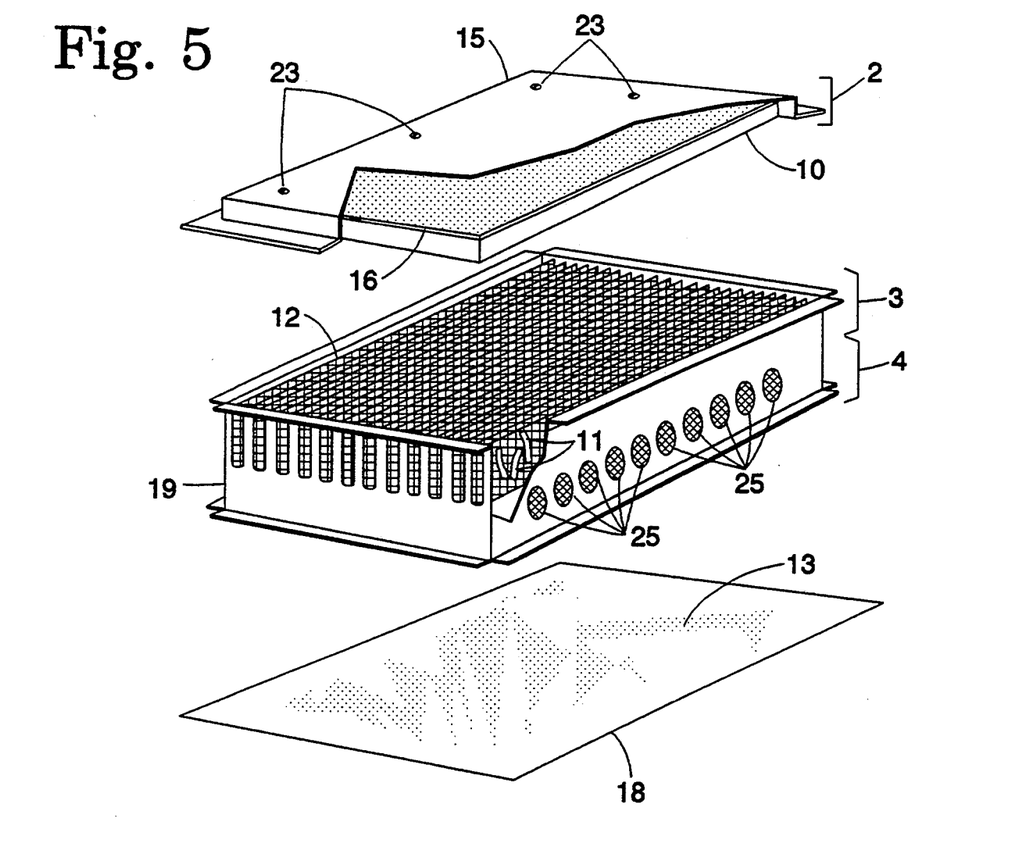
FIG. 5 is a perspective view of another embodiment of a high density rearing unit being used to rear insects for virus production.

The units shown in FIGS. 1 and 5 were generally used for virus production. The unit shown in FIG. 1 was formed from a simple metal rectangle unit 14 (44 cm long, 29 cm wide, and 7 cm high). An area 3 cm high by 42 cm long along the bottom edge of the sides was replaced with screen.

An insert 20 with vertical tabs 21 at each end was constructed from galvanized sheet metal. The tabs 21 were 1 cm wide and 4.5 cm high with slots between successive tabs 21. A piece of ½" hardware cloth (not shown) was placed on top of the insert 20. This helped to keep the diet medium 10 in place during rearing and the large mesh size permitted larvae to feed through and around the cloth.

Partitions 12 consisted of a length of wire screen, fiberglass mesh or polyester waistband stabilizer (4.3 cm wide) strung back and forth from end to end through the slots, as shown in FIG. 2. The waistband stabilizer tended to absorb some moisture and the wire screen stood up better in an autoclave than other substrates. This should be considered in selecting the substrate for the partitions 12.

The partitions 12 can include holes to allow the larvae to disperse, however, a small space between the partitions 12 and the diet medium 10 or frass collection pan 17 or a larger mesh provides a similar effect. The frass-collection tray 3 was simply a 48.5×33 cm piece of galvanized sheet metal. Thus, the assembled rearing unit shown in FIG. 1 comprised the rectangular unit 14 inverted upon the frass-collection sheet 18. This unit 1 contained enough diet 10 and ample space to rear approximately 2500 larvae 11 to pupation.

The diet space 2 of the unit shown in FIG. 5 comprised a 43.8×29.2×2.5 cm tray 15 with a 38.5×27 cm piece of hardware cloth or a perforated aluminum sheet 16 (0.25" hole diameter, 14 gauge) attached to the bottom by screws 23. The tray 15 held 3 liters of diet 10. A metal rectangle 19 (44 cm long, 29 cm wide, and 7.5 cm high) with a flange (1 cm) along the top and bottom edges. The flange along the top of the metal rectangle 19 was a good spacer guide between the partitions 12 and the diet medium 10.

Holes 25 (2.2 cm diameter at 4 cm intervals, 2 cm from the bottom edge) were made along the bottom of the metal rectangle 19. These holes 25 were covered with screen. The assembled rearing unit shown in FIG. 5 comprised the diet tray 15 inverted upon the metal rectangle 19 which itself was set upon the frass-collection sheet 18.

For production of virus, inoculum is applied to the diet medium 10 at a time and concentration appropriate to cause the larvae to die as last instar larvae. The infected larvae are collected just prior to death. One big advantage of this embodiment is that the diet tray 15 can be lifted off of the metal rectangle 19 and the virus inoculum can be applied or the frass collection sheet 18 as well and larvae can be harvested easily by washing down the partitions 12.

Colony Production Unit

Figure 3:
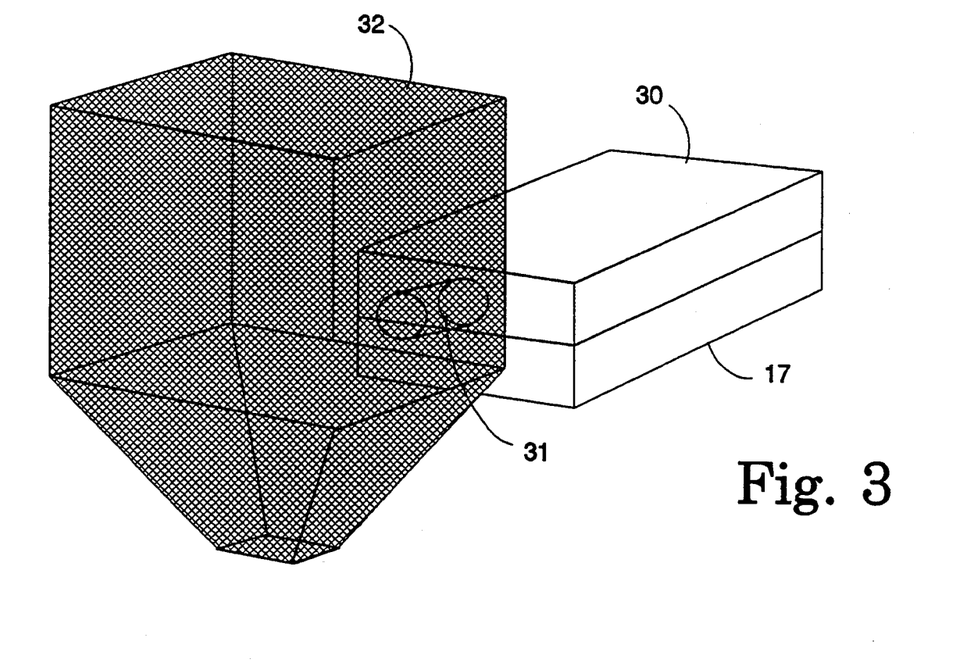
FIG. 3 is a perspective view of one embodiment of a high density rearing unit with an emergence pan connected to an oviposition cage.
Figure 4:
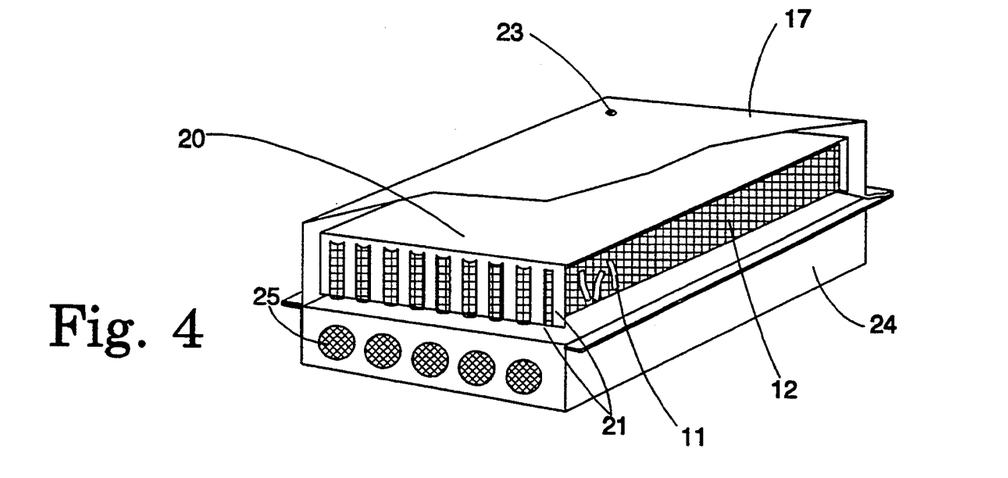
FIG. 4 is a perspective view of one embodiment of a high density rearing unit being used to rear insects for colony production.
Figure 6:
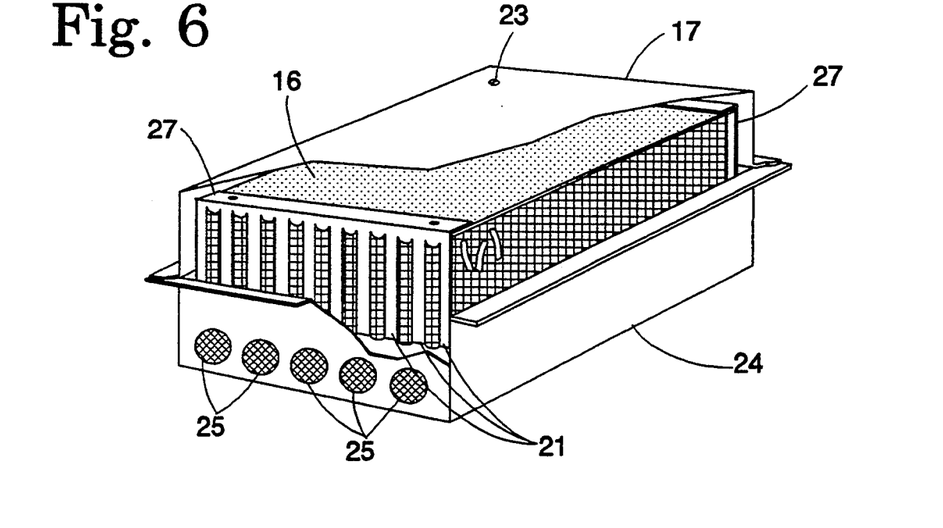
FIG. 6 is a perspective view of another embodiment of a high density rearing unit being used to rear insects for colony production.

FIG. 3 is a perspective view of an embodiment of a high density rearing unit with an emergence pan connected to an oviposition cage. As shown in FIGS. 4 and 6, the diet space 2 and larval space 3 were incorporated in a single 33×23×5 cm aluminum pan 17. The differences between the embodiments shown in FIGS. 4 and 6 is the length of the tabs 21, the width of the partitions 12 and the plates 27.

Either an insert 20 or end pieces 27 were provided with vertical tabs 21. An insert 20 with vertical tabs 21 at each end was constructed from galvanized sheet metal. The tabs 21 were 1 cm wide and 4.5 cm high with 1.1 cm between successive tabs 21 except for two diagonal corners, in which the first two tabs 21 were about 1.5 mm apart creating a narrow spaced tab for maintaining a connection of the distal ends of the partitions 12 to the insert 20. Partitions 12 were strung back and forth around the insert tabs 21.

A piece of ¼" hardware cloth (21×28 cm) or a perforated aluminum sheet 16 was attached to the bottom of the pan 17 by screws 23 or rivets (not shown). This can be held up off the bottom of the pan 17 by folding over the cloth or sheet 16. Washers could be provided between the pan 17 and the cloth or sheet 16.

The frass space 4 was made of the same size aluminum pan 24 with screen covered ventilation holes 25 in the ends. If larvae tend to fall into the frass collection pan 24, mesh or other partition type material can be added to the inside walls of the pan 24 to facilitate larval movement back into the larval space 3.

The entire unit was sterilized (sodium hypochlorite or autoclaving) and dried. Modified high wheat germ diet (1.2 liters) was poured into the pan 17 and allowed to solidify. Sixty to Ninety mg of surface-sterilized *T. ni* eggs in the mandible stage were placed on the diet 10 and a frass collection pan 24 was clipped to the pan 17 using a ⅝" capacity binder clip (not shown) at each corner. The unit was inverted and placed on the shelf of a rearing rack. Initially, tape was covering all of the ventilation holes and was withdrawn as needed to control moisture. Subsequently, the units have been held in an environment with controlled humidity and it is not necessary to cover the vent holes.

When all larvae 11 had pupated, the frass-collecting pan 24 was removed and the diet/larval pan 17 was inverted and covered by an emergence pan 30 made from the same size aluminum pan with a length (4 cm) of Plexiglas tube 31 (4 cm OD, 3.5 cm ID) inserted in the center of one end and screen covered holed on the opposite end (not shown). This unit was joined to an adult oviposition cage 32 by means of the Plexiglas tube 31 so that adults could pass from the larval rearing unit 1 into the oviposition cage 32 as they emerged. The shape of the oviposition cage 32 is not critical other than the fact that it is connected to the tube 31 and does not allow adults to escape.

Edge Posts Embodiments

Figure 7:
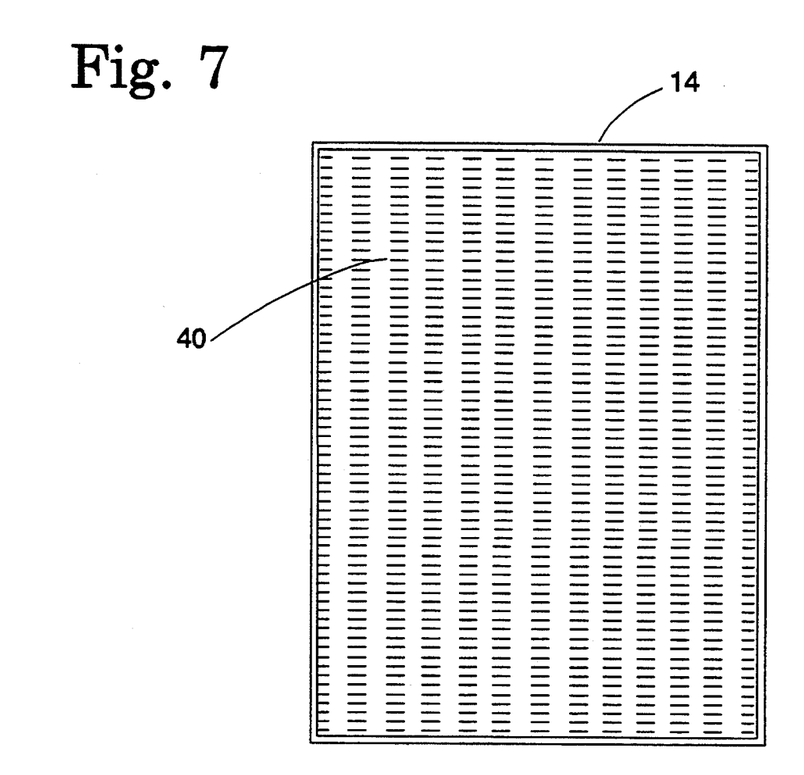
FIG. 7 is a top view of another embodiment of a high density rearing unit showing a configuration of edge posts.

Many leaf-feeding insects feed primarily on the margins rather than on the flat surfaces of the leaves. A strong edge-effect bias appears to be associated with this behavior, i.e., given a choice between standing on a broad surface to feed or standing on an edge to feed, they will strongly prefer the edge. The edge effect can be utilized in the design of a rearing unit to maximize larval density; the larvae are literally lined up side by side in rows feeding on the diet. The strong bias for standing on an edge provides the mechanism for spacing the larvae, reducing interaction between the closely spaced larvae, and effecting the optimal orientation of spacing to maximize the number of larvae per unit surface area of diet. FIG. 7 is a top view of another embodiment of a high density rearing unit showing a configuration of edge posts.

Figure 8:
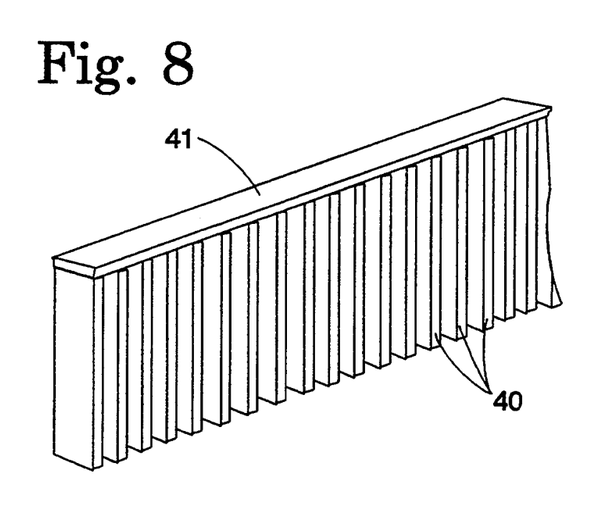
FIG. 8 is a perspective view of one possible formation of a row of edge posts to be used in a high density rearing unit.

Using this edge effect, materials that are not suitable for use as flat partitions are suitable when presented as edges. For example, while the larvae cannot adhere well to polyethylene or metal surfaces, they can hold very well to polyethylene or metal edges. Besides line normal durability advantage, these materials hold up better when autoclaving or sterilizing the unit. Aluminum was used in the units first constructed that implemented this concept while rearing *Tricoplusia ni* larvae. Strips of aluminum were cut and bent to form rows of vertical edge posts 40 parallel to each other and oriented at right angles to the base 41 forming the row as shown in FIG. 8. The posts 40 were 5 mm wide, 5 cm long and spaced about spaced 5 mm apart from each other. The rows were 8 mm apart and extended the full length of the rearing pan. An additional row 2 mm wide was placed against each edge of the rearing pan, providing a total of 2 single-edged rows (along the sides) and sixteen double-edged rows in a 33×23 cm pan. Once the rows of posts 40 were attached to the bottom of the pan, it was not necessary to provide any other means for holding the diet together once the pan is flipped upside down for use.

Figure 9:
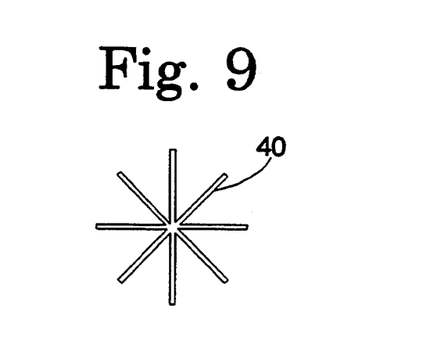
FIG. 9 is a top view of an alternative configuration for an edge post with eight edges for larvae to attach themselves.

Alternative configurations for the edge posts 40 can be designed to provide more edges per post 40. FIG. 9 shows an alternative configuration with eight edges for larvae to attach themselves. The design and placement of the posts 40 can be varied to optimize the larval density within the unit, this would depend greatly upon the size and behavior of species of larvae. The spacing of the tabs and rows can be optimized for the particular species to be reared and stage to which it is to be reared. The spacing described above allows for the rearing of about 2,250 *T. ni* larvae to pupation and adult. The spacing also suits the physical requirements of this species for pupation sites, so the larvae pupate mostly within & between the rows of posts 40 rather than wandering to pupate in other parts of the rearing container such as the frass space. The diet has to be about 2 cm deep and the posts 40 must stick up about 1.5 cm above the diet, so the posts 40 could be shortened to about 3.5 cm and the total unit could be as short as 5 cm, leaving 1.5 cm as a frass space. This would provide a larval density of about 14,000 larvae per cubic foot.

Figure 10:
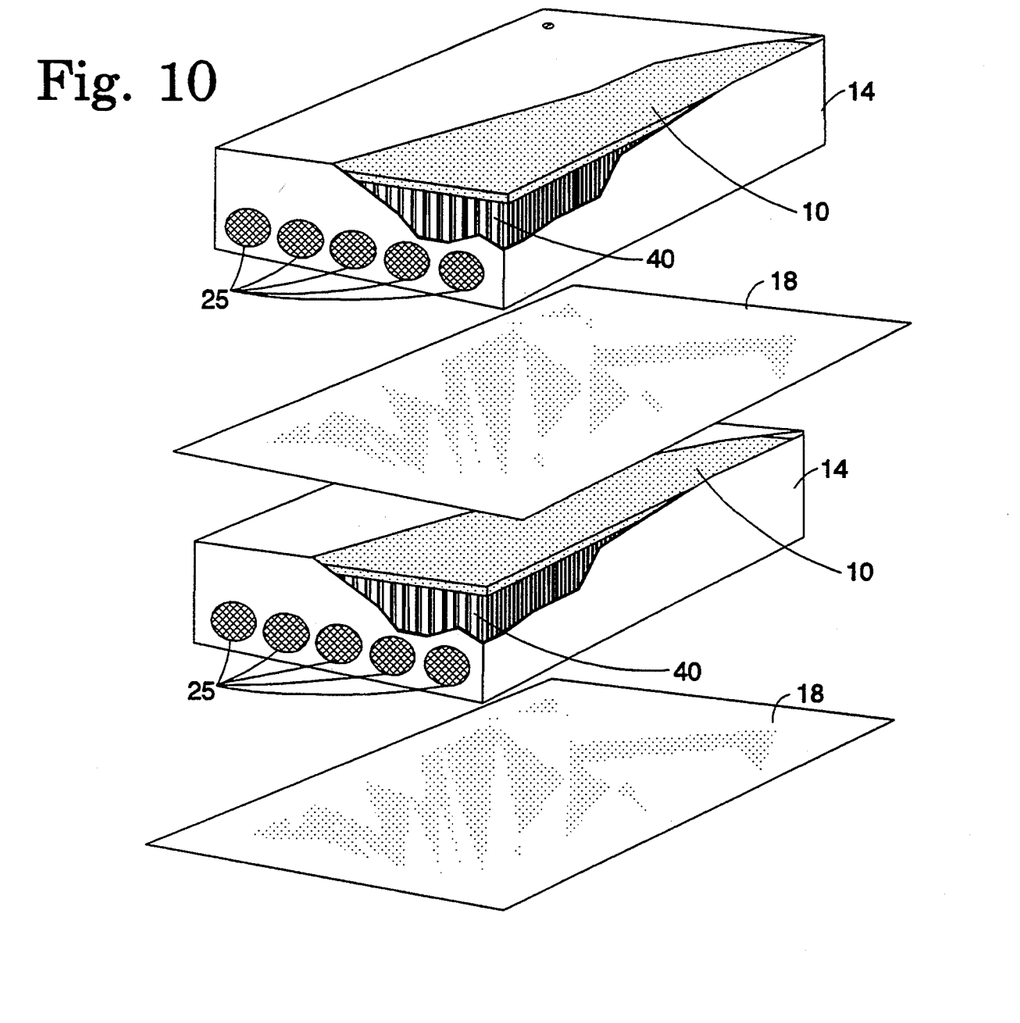
FIG. 10 is a perspective view of the multiple high density rearing units being stacked on top of one another illustrating the compact nature of the units.

FIG. 10 shows multiple high density rearing units being stacked on top of one another illustrating the compact nature of the units. The top of one unit could be the bottom of the next such that the frass collection sheet would be eliminated or replaced by the top of the unit underneath. By using the teachings of the present invention, massive numbers of larvae can be reared at very high densities.

Example of Virus Production

Larvae were reared in the rearing unit until they molted into the last instar (9 days after hatch under these conditions). At that time, the virus suspension was sprayed over the diet medium 10 and larvae 11. The treated unit was then held in an incubator until about 1% of the treated larvae were liquefying (about 3 days after treatment). The larvae were harvested into a container and their total fresh weight was measured. They were frozen until the virus was extracted.

Fifty grams fresh weight of diseased larvae were blended in a Waring blender with 160 ml of water. The slurry was put into a 200 ml centrifuge bottle and centrifuged at 5,000 rpm for 15 minutes. The pellet was resuspended in 100 ml of 1% sodium dodecyl sulfate (SDS)

and then centrifuged again at 5,000 rpm for 15 minutes. The pellet was then resuspended to a total volume of 45 ml and thoroughly mixed by sonication and vortexing. Ten-fold dilutions were made in water and the number of polyhedra counted with a hemacytometer. Three independent dilution series were made for each sample and counts were made on a given series until the coefficient of variation was less than or equal to 10%.

Without optimizing the system, a yield of 200–250 g of diseased larvae were obtained from the small (colony) unit. Application of approximately $3 \times 10^6$ polyhedra to the small unit (about 680 cm$^2$ surface area) yielded about $7 \times 10^{11}$ to $1 \times 10^{12}$ polyhedra. As expected, yields from the large unit averaged about 2.5 times those from the small unit with only a 90% increase in diet surface area.

The foregoing description has been directed to particular embodiments of the invention in accordance with the requirements of the Patent Statutes for the purposes of illustration and explanation. It will become apparent, however, to those skilled in the art that many modifications, variations and changes will be possible without departure from the scope and spirit of the invention. It is intended that the following claims be interpreted to embrace all such modifications.

I claim:

1. A method of rearing insect larvae, comprising the following steps:
   a. providing an enclosed rearing unit located within an appropriate environment for rearing said insect larvae;
   b. providing a diet space within said rearing unit including an appropriate diet medium for said insects;
   c. providing a larval space within said rearing unit located below said diet space and including larval attaching surfaces such that said insect larvae are able to disperse themselves over said surfaces;
   d. providing a frass space within said rearing unit located below said larval space wherein any frass collects within said frass space as it is produced and does not interfere with said larval space or said diet space;
   e. determining a maximum larval density for said insect larvae within said rearing unit at a particular desired stage of larval development wherein said maximum larval density is based upon spatial behavior of said insect larvae and the amount of said surfaces within said larval space;
   f. placing eggs of said insect larvae or early stage insect larvae within said rearing unit such that any emerging larvae from said eggs or early stage insect larvae are able to move into said larval space of said rearing unit and the amount of eggs or early stage insect larvae placed within said rearing unit is dependant upon the maximum larval density for said insect larvae; and
   g. allowing said larvae to grow to said desired stage of development.

2. The method of claim 1 wherein said frass space is provided with means for controlling air passage through said rearing unit such that said insect larvae can not escape through said means for controlling air passage yet excess moisture from said frass can escape.

3. The method of claim 1 wherein said insect larvae are lepidopterous insects.

4. The method of claim 1 wherein said rearing unit includes a removable frass collection pan and said method further comprises the steps of:
   h. replacing said frass collection pan with an emergence pan including an outlet for allowing emerging insects, formerly pupated insect larvae, to enter an oviposition cage; and
   i. inverting said rearing unit when all of said larvae have pupated such that said emergence pan is located above said larval space and said diet space.

5. The method of claim 1 further comprising the step of applying viral inoculum to the diet medium at a time and concentration appropriate to cause the larvae to die as last instar larvae.

6. The method of claim 1 wherein said larval attaching surfaces are provided by vertical edge posts perpendicular to said diet such that said larvae attach themselves to said edge posts.

7. The method of claim 1 wherein said larval attaching surfaces are provided by a series of vertical partitions perpendicular to and in contact with or nearly in contact with said diet medium.

8. An insect larvae rearing system, comprising:
   a. an enclosed rearing unit;
   b. a diet space within said rearing unit including an appropriate diet medium for said insect larvae;
   c. a larval space within said rearing unit located below said diet space and including larval attaching surfaces such that said insect larvae are able to disperse themselves over said surfaces; and
   d. a frass space within said rearing unit located below said larval space wherein any frass collects within said frass space as it is produced and does not interfere with said larval space or said diet space.

9. The rearing system of claim 8 wherein said frass space is provided with means for controlling air passage through said rearing unit such that said insect larvae can not escape through said means for controlling air passage yet excess moisture from said frass can escape.

10. The rearing system of claim 8 wherein said rearing unit includes side walls which provide a substrate for emerging larvae to move across and into said larval space of said rearing unit.

11. The rearing system of claim 8 wherein said enclosed rearing unit includes a removable frass collection pan.

12. The rearing system of claim 11 further comprising an emergence pan including an outlet for allowing emerging adults, formerly pupated insect larvae, to enter an oviposition cage wherein said emergence pan replaces said frass collection pan when all of said larvae have pupated and said rearing unit is turned upside down such that said emergence pan is located above said larval space and said diet space.

13. The rearing unit of claim 8 wherein said larval attaching surfaces are vertical edge posts perpendicular to said diet such that said larvae attach themselves to said edge posts.

14. The rearing unit of claim 8 wherein said larval attaching surfaces are a series of vertical partitions perpendicular to and in contact with or nearly in contact with said diet medium.

15. A method of producing virus, comprising the following steps:
   a. providing an enclosed rearing unit located within an appropriate environment for rearing insect larvae;

b. providing a diet space within said rearing unit including an appropriate diet medium for said insects;

c. providing a larval space within said rearing unit located below said diet space and including larval attaching surfaces such that said insect larvae are able to disperse themselves over said surfaces;

d. providing a frass space within said rearing unit located below said larval space wherein any frass collects within said frass space as it is produced and does not interfere with said larval space or said diet space;

e. determining a maximum larval density for said insect larvae within said rearing unit at a particular desired stage of larval development for inoculation wherein said maximum larval density is based upon spatial behavior of said insect larvae and the amount of said surfaces within said larval space;

f. placing eggs of said insect larvae or early stage insect larvae within said rearing unit such that any emerging larvae from said eggs or early stage insect larvae are able to move into said larval space of said rearing unit and the amount of eggs or early stage insect larvae placed within said rearing unit is dependant upon the maximum larval density for said insect larvae;

g. allowing said larvae to grow to said desired stage of development;

h. inoculating said larvae with said virus by spraying a vital suspension including said virus over at least said diet medium; and i. harvesting said virus from said larvae once said inoculated larvae are sufficiently infected by said virus.

16. The method of claim 15 wherein said frass space is provided with means for controlling air passage through said rearing unit such that said insect larvae can not escape through said means for controlling air passage yet excess moisture from said frass can escape.

17. The method of claim 15 wherein said insect larvae are lepidopterous insects.

18. The method of claim 15 wherein said extraction of virus, comprises the steps of:
  1. blending said harvested larvae with water to form a slurry,
  2. centrifuging said slurry to form a first pellet,
  3. pouring off any non-pellet material after centrifuging and resuspending said first pellet in a solution of sodium dodecyl sulfate,
  4. centrifuging said resuspending pellet to form a second pellet, and
  5. resuspending said second pellet to form a suspension of said virus.

19. The method of claim 15 wherein said larval attaching surfaces are provide by vertical edge posts perpendicular to said diet such that said larvae attach themselves to said edge posts.

20. The method of claim 15 wherein said larval attaching surface are provided by a series of vertical partitions perpendicular to and in contact with or nearly in contact with said diet medium.

* * * * *